US00PP32932P2

(12) United States Plant Patent
Read

(10) Patent No.: US PP32,932 P2
(45) Date of Patent: Mar. 30, 2021

(54) ***ACHILLEA* PLANT NAMED 'LEMON CHERRY FIZZ'**

(50) Latin Name: *Achillea millefolium*
Varietal Denomination: Lemon Cherry Fizz

(71) Applicant: Realflor, Bognor Regis (GB)

(72) Inventor: Charles Richard Read, Bognor Regis (GB)

(73) Assignee: Realflor, Bognor Regis (GB)

( * ) Notice: Subject to any disclaimer, the term of this patent is extended or adjusted under 35 U.S.C. 154(b) by 0 days.

(21) Appl. No.: 16/914,415

(22) Filed: Jun. 28, 2020

(51) Int. Cl.
*A01H 5/02* (2018.01)
*A01H 6/14* (2018.01)

(52) U.S. Cl.
USPC ..... Plt./263.1
CPC ..... *A01H 6/14* (2018.05)

(58) Field of Classification Search
USPC ..... Plt./263.1
CPC ..... A01H 6/14; A01H 5/02
See application file for complete search history.

*Primary Examiner* — Keith O. Robinson
(74) *Attorney, Agent, or Firm* — Weatherly IP Solutions, LLC; Barbara Campbell

(57) ABSTRACT

A new variety of *Achillea* plant named 'Lemon Cherry Fizz' that is distinguishable by basal branching, soft fern-like foliage which is yellow-green in color, and inflorescences which consist of red ray flowers becoming darker with age, and disc flowers with strongly exserted yellow stamens. Flowering of 'Lemon Cherry Fizz' commences in April and continues until October on plants which are 40 cm to 45 cm in height and 40 cm in width after 1 year of growth from an initial cutting.

2 Drawing Sheets

Genus and species: *Achillea millefolium.*
Variety denomination: 'Lemon Cherry Fizz'.

BACKGROUND OF THE NEW PLANT

The present invention relates to a new and distinct cultivar of *Achillea* commonly known as Yarrow, which is grown as an ornamental plant for use in the garden and landscape. The new cultivar is known botanically as *Achillea millefolium* and will be referred to hereinafter by the cultivar name 'Lemon Cherry Fizz'.

*Achillea* is a genus within the family Asteraceae in which the commonly referred to "flower" is botanically the inflorescence which is comprised of outer showy ray florets surrounding smaller disc florets. The inflorescences of *Achillea* are borne in clusters or corymbs.

'Lemon Cherry Fizz' arose and was selected from an ongoing breeding program which is conducted by the inventor at the inventor's greenhouse and nursery in South Mundham, West Sussex, United Kingdom. The breeding program commenced in 2015 with the aim of developing new and improved commercial varieties of *Achillea*. Each year's breeding cycle consists of controlled pollination between chosen male and female parents including unnamed and unreleased seedlings retained from previous breeding cycles. Seed from each year's cycle is harvested and sown in the fall, and new seedlings are raised and evaluated in the following summer.

'Lemon Cherry Fizz' is a seedling selection that resulted from the controlled pollination in 2015 of a single plant of the inventor's proprietary *Achillea* seedling code 'Ac 1400-5' (unreleased and unpatented) as the female parent, using pollen from a single plant of the inventor's proprietary *Achillea* seedling code 'Ac 1400-3' (unreleased and unpatented) as the male parent. The inventor selected 'Lemon Cherry Fizz' in 2015 for its unique yellow-green foliage color and vivid red blooms which are borne above the foliage in massed flattened dome-shaped corymbs.

'Lemon Cherry Fizz' was first asexually propagated by the inventor in South Mundham, West Sussex, United Kingdom using the method of shoot tip cuttings. Since that time under careful observation 'Lemon Cherry Fizz' has been determined uniform, stable and true to type in subsequent generations of asexual propagation via shoot tip cuttings.

SUMMARY

The following traits have been repeatedly observed and represent the distinguishing characteristics of 'Lemon Cherry Fizz'. In combination, these traits set 'Lemon Cherry Fizz' apart from all other existing varieties of *Achillea* known to the inventor. 'Lemon Cherry Fizz' has not been tested under all possible conditions and phenotypic differences may be observed with variations in environmental, climatic, and cultural conditions, however, without any variance in genotype.

1. 'Lemon Cherry Fizz' exhibits tight clumping basal-branching plant habit.
2. The young foliage of 'Lemon Cherry Fizz' is yellow-green in color, becoming darker, but still yellow-green, when the foliage is mature and fully expanded.
3. The foliage of 'Lemon Cherry Fizz' is finely dissected and fern-like in appearance and soft in texture.
4. A fully expanded corymb of 'Lemon Cherry Fizz' is 8 cm to 9 cm in diameter and is comprised of inflorescences which contain ray florets arranged around a central disc.
5. The ray florets of 'Lemon Cherry Fizz' are arranged in the corymb to form a flattened dome.

6. The ray florets of 'Lemon Cherry Fizz' are red in color, becoming deeper red with age.
7. The mass of disc florets of 'Lemon Cherry Fizz' exhibit tiny red petals and strongly exserted prominent yellow stamens.
8. Flowering of 'Lemon Cherry Fizz' commences in April with full flowering by mid-late June and continuing until October.
9. After one year of growth in a 2-gallon container, or planted in the ground, a plant of 'Lemon Cherry Fizz' is 40 cm to 45 cm in height (including the flowers) and 40 cm in width.
10. 'Lemon Cherry Fizz' is hardy in USDA Zone 3 (−40° F. or −40° C.).

BRIEF DESCRIPTION OF THE PHOTOGRAPHS

The accompanying color photographs illustrate the overall appearance of 'Lemon Cherry Fizz' showing the color of foliage and inflorescence as true as is reasonably possible to obtain in color reproductions of this type. The photographs were taken from plants which were growing outdoors in Oxnard, Calif., without any pruning or use of chemical growth regulators. The colors in the photographs may differ from color values cited in the detailed botanical description, which accurately describe the colors of 'Lemon Cherry Fizz'.

BOTANICAL DESCRIPTION OF THE PLANT

Figure 1:
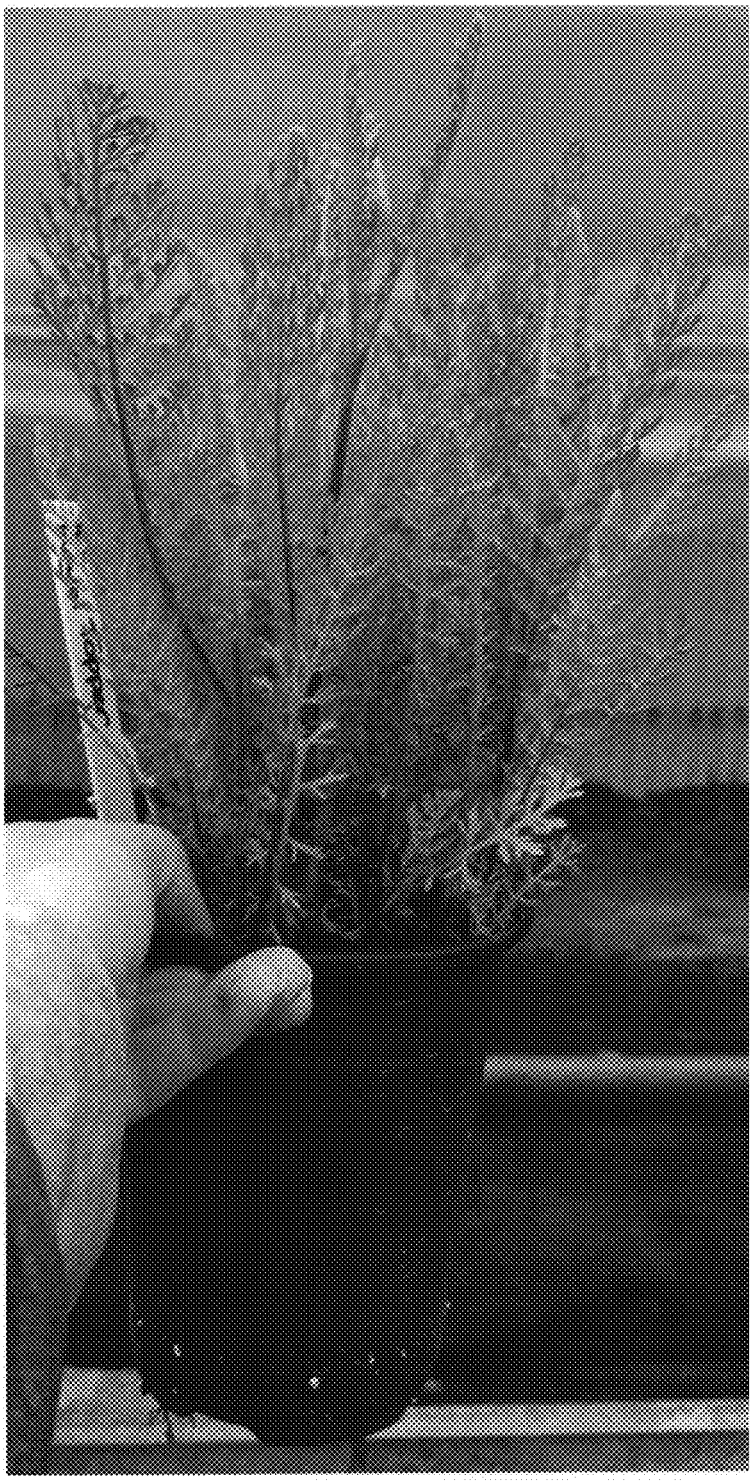
FIG. 1 is a photograph of a plant of 'Lemon Cherry Fizz' which was potted in spring in Oxnard, Calif. and grown through the summer months. No flowers have been formed at this stage.
Figure 2:
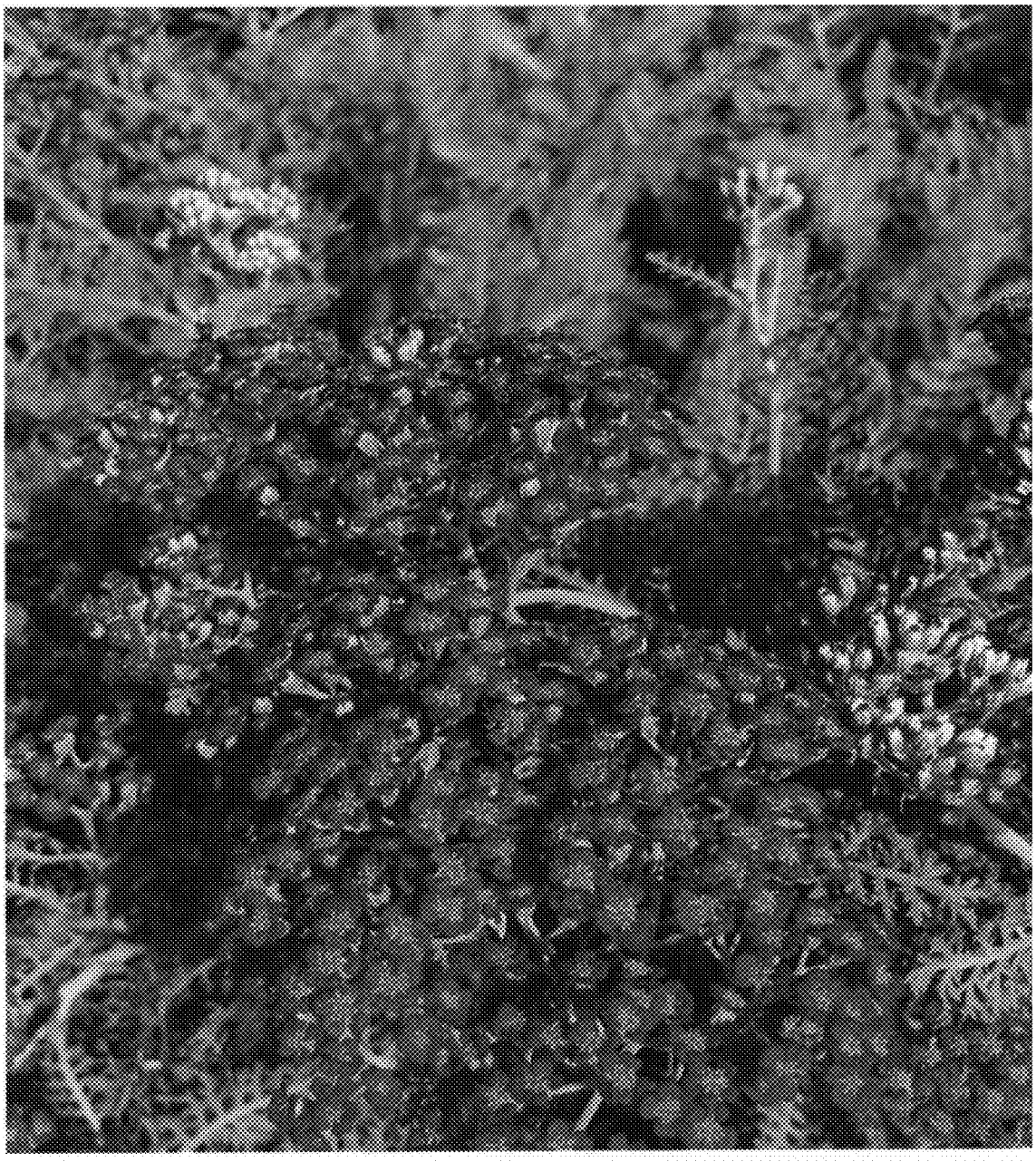
FIG. 2 is a photograph of 'Lemon Cherry Fizz' that shows the buds and open flowers of the inflorescences of 'Lemon Cherry Fizz' in late June. The plant had been planted in late summer in open ground in Oxnard, Calif., and grown through the winter for vernalization and early summer flowering.

The following is a detailed botanical description of the new cultivar 'Lemon Cherry Fizz'. Observations, measurements, values and comparisons were collected in Oxnard, Calif. during late June 2020 from a 1-year old plant growing in-ground outdoors. Color determinations are made in accordance with The 2007 Royal Horticultural Society Colour Chart from London, England, except where general color terms of ordinary dictionary significance are used.

Botanical classification:

*Family*.—Asteraceae.
*Genus*.—*Achillea*.
*Species*.—*Millefolium*.
*Denomination*.—'Lemon Cherry Fizz'.
*Common name*.—Yarrow.
*Habit*.—Basal-branching, upright and spreading.
*Commercial category*.—Perennial.
*Use*.—For garden and landscape.
*Suggested commercial container size*.—4-inch, 1 gallon, 2-gallon containers.
*Parentage*.—*Achillea millefolium* 'Lemon Cherry Fizz' is a seedling selection resulting from the controlled cross-pollination of the following parents — Female parent: inventor's proprietary *Achillea* seedling code 'Ac 1400-5'. Male parent: inventor's proprietary *Achillea* seedling code 'Ac 1400-3'.
*Propagation method*.—Shoot tip cuttings.
*Rooting system*.—Fine and fibrous.
*Time to develop roots* (*range*).—14 to 21 days are needed for an initial cutting to develop roots.
*Temperature to develop roots* (*range*).—The recommended air temperature is 20° C. to 21° C.
*Crop time* (*from planting a rooted cutting*).—14 weeks to produce a flowering plant in a 1-gallon container.
*Plant dimensions* (*one year*).—40 cm to 45 cm in height (including the flowers) and 40 cm in width.
*Cultural requirements*.—Grow in full sun and rich, moist moderately fertile well-draining soil.
*Vernalization requirements*.—Vernalization is not required for 'Lemon Cherry Fizz' to flower in the following spring and summer. However, vernalization will promote earlier and more prolific flowering in the following spring and summer.
*Pest or disease resistance and susceptibility*.—Deer resistant and salt tolerant. Otherwise, no specific disease or pest resistance or susceptibility has been observed.
*Hardiness*.—USDA Zone 3.

Stem:

*Branching*.—Basal stems and secondary branching stems.
*Basal stems*.—Typically, 12 to 15 stems arise from the base of which 5 to 8 stems will bear flowers in large corymbs.
*Secondary stems*.—As it matures, each basal stem produces short lateral stems which bear small corymbs of flowers.
*Stem shape*.—Cylindrical.
*Stem dimensions*.—Basal stems 20 cm to 25 cm in length, 5 mm in diameter at base. Secondary stems up to 12 cm in length, 3 mm to 4 mm in diameter.
*Stem surfaces*.—Lightly pubescent.
*Stem color* (*basal stems*).—Brown-purple 187A except for new growth yellow-green 144C.
*Stem color* (*secondary stems*).—144C.

Foliage:

*Type* (*division*).—Pinnatifid. Very finely dissected into approximately 25 pairs of opposite leaflets.
*Arrangement*.—Alternate, slightly offset (3 mm to 4 mm) pairs.
*Internode length* (*range*).—8 mm to 12 mm.
*Margin*.—Entire.
*Apex*.—Acute.
*Base*.—Truncate.
*Leaf and leaflet attachment*.—Sessile.
*Leaf and leaflet angle*.—Acute, close to 45 degrees, between adaxial surface and stem.
*Leaf and leaflet color*.—Ranges between 150B (young foliage growth) and 144C (mature foliage growth).
*Leaf shape*.—Lanceolate.
*Leaf dimensions*.—25 mm to 40 mm in length, 15 mm in width at base.
*Leaflet shape*.—Trilobed, sessile to leaf.
*Leaflet dimensions*.—Up to 10 mm in length, 4 mm in width.
*Leaf and leaflet venation*.—Pinnate.
*Vein color* (*both surfaces*).—Indistinguishable from leaf color.
*Leaf surface* (*both surfaces*).—Puberulent.
*Leaf texture*.—Soft.

Inflorescence:

*Inflorescence type.*—Indeterminate compound corymb consisting of small single inflorescences comprising ray florets, disc florets, receptacle and phyllaries.

*Corymb quantity per plant.*—25 to 30.

*Corymb shape.*—Flattened dome.

*Corymb dimensions.*—8 cm to 9 cm in width, 1 cm to 2 cm in height (above the peduncles).

*Corymb peduncle dimensions (from stem to pedicels)*.—2 cm to 3 cm in length, 1.5 mm to 2.0 mm in diameter.

*Peduncle shape.*—Cylindrical.

*Peduncle color.*—138C.

*Peduncle surface.*—Lightly pubescent; hairs fine, white, less than 0.5 mm in length.

*Inflorescence pedicels.*—Dimensions: 6 mm to 8 mm in length, 1 mm in diameter. Pedicel color: 138C. Pedicel surface: Lightly pubescent; hairs fine, white, less than 0.5 mm in length.

*Inflorescence quantity per corymb (average).*—120.

*Inflorescence diameter (ray flowers fully opened).*—6 mm.

*Inflorescence depth.*—2 mm.

*Inflorescence aspect.*—Upright.

*Inflorescence colors (when fully developed).*—Ray florets: Ranges between 46A and 46B, aging to 60A. Disc florets: 46A, exserted stamens 23B.

*Fragrance.*—Musty.

*Blooming season.*—Commences in April with full flowering by mid-late June and continuing until October.

*Lastingness of inflorescence (range).*—10 to 14 days on the plant, persistent.

Bud:

*Shape.*—Ovoid, ribbed longitudinally.

*Dimensions.*—2.5 mm in diameter, 3.0 mm in height.

*Color.*—138C.

*Surface.*—Glabrous.

Ray florets:

*Ray floret arrangement.*—Rotate, single whorl.

*Quantity.*—5 per inflorescence.

*Aspect.*—Horizontal.

*Corolla tube dimensions.*—2.5 mm in length, 1.5 mm in diameter.

*Corolla tube color (both surfaces).*—157C.

Ray floret petals:

*Shape.*—Bilobed, lobes fused adjacent, each lobe semicircular.

*Dimensions (both lobes together).*—2.5 mm in height, 3 mm in width.

*Surface.*—Glabrous (both surface); abaxial surface presents raided midrib.

*Apex (each petal lobe).*—Tiny, acuminate, approximately 0.5 mm in length and width.

*Margin.*—Entire.

*Color (adaxial surface).*—Ranges between 46A and 46B.

*Color (abaxial surface).*—As adaxial surface except midrib and base 160B.

Disc florets:

*Disc diameter.*—2.5 mm.

*Disc color (mass of disc florets).*—46A (visible floret apices), 23B exserted stamens.

*Disc floret quantity.*—12.

*Disc floret shape.*—Tubular.

*Disc floret dimensions.*—5 mm in length (including corolla tube), 1 mm in diameter.

*Disc floret corolla.*—5-lobed, color 157C.

*Disc floret petals.*—5, very small. Dimensions: 0.5 mm in length and width. Color (both surfaces): 46A. Surface (both surfaces): glabrous. Apex: Rounded. Base: Truncate.

*Margin.*—Smooth, entire.

Receptacle:

*Shape.*—Flattened dome.

*Dimensions.*—3 mm to 4 mm in diameter, 2.5 mm in height.

*Color.*—144C.

Phyllaries:

*Description.*—Appear as paper-like bracts or scales which subtend the ray florets and the outermost disc florets.

*Arrangement.*—Two concentric whorls.

*Quantity.*—16 to 20.

*Shape.*—Lanceolate.

*Dimensions.*—2 mm in length, 1 mm in width.

*Apex.*—Acute.

*Base.*—Truncate.

*Margins.*—Entire.

*Surface texture (both surfaces).*—Glabrous.

*Color (both surfaces).*—138C.

Reproductive organs:

*Ray flowers.*—Androecium (stamens, filaments, anthers, pollen): Absent. Gynoecium: Pistil: 1, 3 mm in length, diameter is less than 0.5 mm. Stigma: Bifid, 1 mm in length, color 157C. Style: Cylindrical, 1.5 mm in length, less than 0.5 mm in diameter, color 157D.

*Disc flowers.*—Androecium: Stamens: 5, bifid. Stamen color (where exserted and anthers) 23B. Stamen filaments: Length 2 mm, diameter less than 0.5 mm, color 157D. Anthers: Borne on exserted stamens, cylindrical, length 2 mm, diameter 0.5 mm, color 23B. Pollen: None observed. Gynoecium: Style: Bifid, cylindrical, 2 mm in length, less than 0.5 mm in diameter, color 157D. Stigma: Bifid, cylindrical, 1 mm in length, less than 0.5 mm in diameter, color 157D. Ovary (observed immature only): Inferior, ovate, length less than 1 mm, diameter less than 0.5 mm, color 157D.

Seed: None observed to date.

COMPARISON WITH PARENTAL LINES AND KNOWN VARIETY

'Lemon Cherry Fizz' may be compared with its parents and with all other varieties of *Achillea* known to the inventor, chiefly by foliage color. Whereas the foliage of 'Lemon Cherry Fizz' is yellow-green in color, the foliage of both parents is mid-green in color, as is typical of varieties in the genus. In addition, the flowers of 'Lemon Cherry Fizz' and the female parent 'Ac 1400-5' are red in color, whereas the flowers of the male parent 'Ac 1400-3' are deep pink in color.

Many commercial varieties of *Achillea* exhibit a red flower color which is similar to the color of the flowers of 'Lemon Cherry Fizz'. However, no varieties are known to the inventor which exhibit yellow-green colored foliage. Varieties with similar red-colored flowers include *Achillea* 'Red Velvet' (unpatented), *Achillea* 'Paprika' (unpatented) and *Achillea* 'Balvinred' (U.S. Plant Pat. No. 25,618). All of these varieties exhibit green foliage.

I claim:

1. A new and distinct cultivar of *Achillea* plant named 'Lemon Cherry Fizz' as described and illustrated herein.

* * * * *